United States Patent [19]

Kadaba

[11] Patent Number: 5,648,369

[45] Date of Patent: Jul. 15, 1997

[54] AMINOALKYLPYRIDINE COMPOUNDS WHICH ARE USEFUL AS ANITCONVULSANT DRUGS, EXCITATORY AMINO ACID INHIBITORS AND NMDA SIGMA RECEPTOR ANTAGONISTS

[75] Inventor: Pankaja K. Kadaba, Lexington, Ky.

[73] Assignee: University of Kentucky Research Foundation, Lexington, Ky.

[21] Appl. No.: 793,725

[22] Filed: Nov. 20, 1991

[51] Int. Cl.$^6$ .......................... C07D 213/02; A61K 31/44
[52] U.S. Cl. ............................ 514/357; 546/329; 546/334
[58] Field of Search ........................ 546/329, 334; 514/357

[56] References Cited

U.S. PATENT DOCUMENTS

| | | | |
|---|---|---|---|
| 3,522,262 | 7/1970 | Berger | 546/336 |
| 3,654,290 | 4/1972 | Berger | 546/337 |
| 4,358,466 | 11/1982 | Haken et al. | 546/336 |

OTHER PUBLICATIONS

Roger J. Porter, et al, "Antiepileptic Drug Development Program" The Cleveland Clinic Quarterly, vol. 51, No. 2, Summer 1984, pp. 293–305.

Dennis W. Choi, "Methods for Antagonizing Glutamate Neurotoxicity" Cerebrovasc Brain Metab Rev. vol. 2, No. 2, 1990, pp. 105–147.

*Primary Examiner*—C. Warren Ivy
*Assistant Examiner*—Zinna N. Davis
*Attorney, Agent, or Firm*—Lowe, Price, LeBlanc & Becker

[57] ABSTRACT

Pharmaceutical compositions comprise as the active ingredient potent orally active, nonneurotoxic anticonvulsant compounds that are excitatory amino acid and NMDA/sigma receptor antagonists and that are selected from the group consisting of those of the formulae:

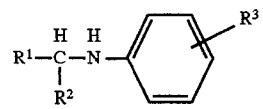

wherein $R^1$ is 4-pyridyl or 3-pyridyl, $R^2$ is hydrogen or methyl and $R^3$ is 3,4-dichloro, p- or m-chloro, p-bromo, p-fluoro, p-methyl, p-methoxy or hydrogen. The compositions are administered to mammals in an amount to provide a dosage amount ranging from about 15 mg/kg to 200 mg/kg.

22 Claims, 1 Drawing Sheet

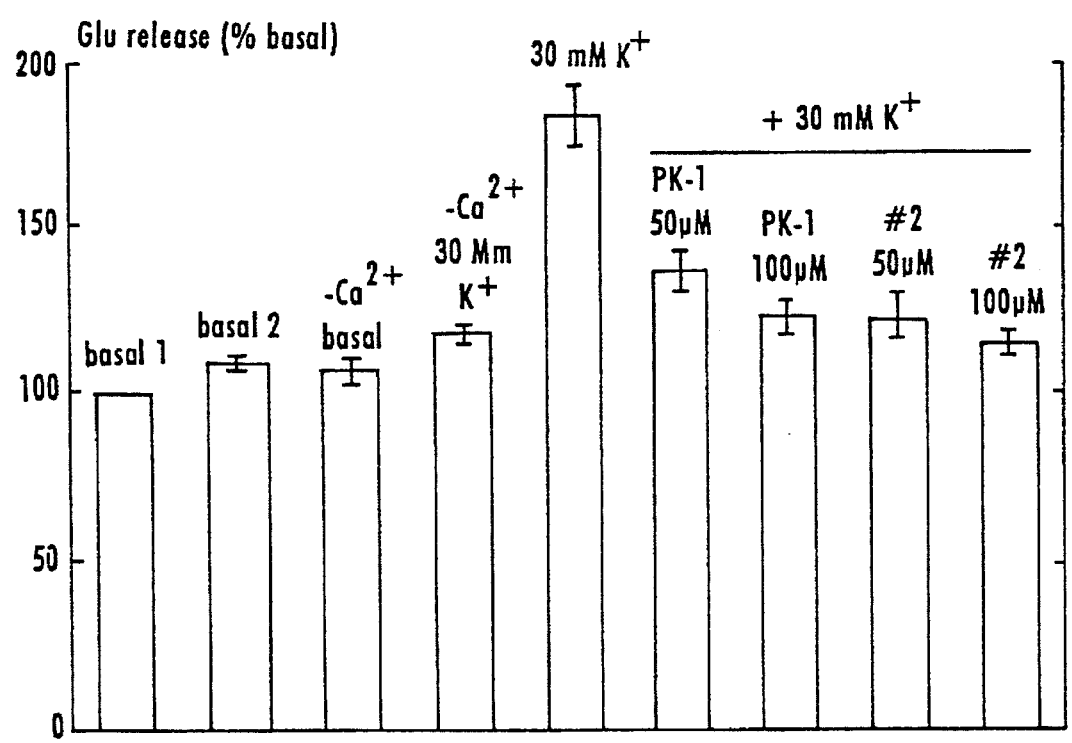

AMINOALKYLPYRIDINE COMPOUNDS WHICH ARE USEFUL AS ANITCONVULSANT DRUGS, EXCITATORY AMINO ACID INHIBITORS AND NMDA SIGMA RECEPTOR ANTAGONISTS

FIELD OF THE INVENTION

This invention relates to novel aminoalkylpyridines and their method of preparation, and more particularly relates to novel aminoalkylpyridines which are useful as excitatory amino acid inhibitors and as NMDA/σ (sigma) receptor antagonists and potent orally active antiepileptic pharmaceutical compositions.

BACKGROUND ART

Epilepsy is a leading neurological disorder, second only to stroke. One to four million Americans and twenty to forty million people world-wide suffer from some form of epilepsy, making it second only to stroke as the leading neurological disorder. Although standard therapy permits control of seizures in 80% of these patients, one-half million people in the U.S. have uncontrolled epilepsy. The number of drugs useful for the treatment of epilepsy is remarkably small. Fewer than 20 drugs are currently marketed in the U.S., and of these, only five or six are widely used. Complex partial epilepsy (also known as temporal lobe, psycomotor or limbic epilepsy), the most devastating form among adults, and estimated to account for an many as two-thirds of all cases, is refractory to drug treatment (Gummit, R. J., "The Epilepsy Handbook, The Practical Management of Seizures", Raven Press, New York, 1983). It is becoming increasingly evident that significant progress toward complete control can be achieved only by an understanding of the mechanisms of the epilepsies themselves, which will provide the molecular basis for antiepileptic drug design and development, and new treatment strategies. Out of the twenty or so new drugs that are in clinical trial in the U.S., only a few have been developed based on the knowledge of epilepsy mechanisms (Dichter, M. A., Epilepsia, 30, S3–S12, 1989).

NMDA receptor overstimulation by high levels of the excitatory amino acid (EAA), L-glutamate, has been implicated in epileptogenesis and epilepsy (Cavalheiro, et al., "Frontiers in Excitatory Amino Acid Research", A. R. Liss, New York, 1988). Thus, development of agents that are EAA/NMDA antagonists may constitute novel and effective therapies for the epilepsies. Although a number of excitatory amino acid (EAA) inhibitors have been discovered, many lack NMDA receptor specificity and are too toxic for clinical studies (Porter, Epilepsia, 30, S29–34, 1989). Thus, the discovery of this invention of certain aminoalkylpyridines as a superior class of anticonvulsant agents in the Applicant's laboratories is significant. The aminoalkylpyridines of this invention are potent, orally active, nonneurotoxic NMDA antagonists that hold promise for commercial development as nontoxic, clinically useful antiepileptic drugs. They can provide the basis for the design of safer NMDA antagonists with increased potency and reduced toxicity for the management of epilepsy in humans.

Certain aminoalkylpyridines are known to the art as described in U.S. Pat. Nos. 4,358,446, 3,522,262, and 3,654,290. Aminoalkyl-3-pyridines are described in U.S. Pat. No. 4,358,446 as intermediates in the preparation of certain N-acylaminoalkyl-3-pyridine derivatives that have activity as fungicides. U.S. Pat. Nos. 3,522,262 and 3,654,290, describe aminoalkylpyridines as intermediates for preparation of certain indole derivatives which have antiallergic activity.

SUMMARY OF THE INVENTION

It is accordingly one object of the present invention to provide novel aminoalkylpyridines and their method of preparation.

It is a further object of the present invention to provide anticonvulsant agents which comprise aminoalkylpyridines.

A further object of the present invention is to provide a method for the treatment of convulsive disorders by administration of an effective amount of the aminoalkylpyridines of this invention.

A further object of the present invention is to provide compounds belonging to two series of aminoalkylpyridine structures and methods for their use in the treatment of neurological disorders such as epilepsy and stroke.

A still further object of the present invention is to provide new aminoalkylpyridines that are inhibitors of the excitatory amino acid (EAA) neurotransmitter L-glutamate. The aminoalkylpyridines of this invention produce a significant inhibition of the presynaptic release of L-glutamate and also act as noncompetitive NMDA antagonists by selectively inhibiting the specific binding of the radioligand [$^3$H]DTG (ditolylguanidine) to σ (sigma) receptor sites on the N-methyl-D-aspartate (NMDA) receptor complex in the brain.

A still further object of the present invention is to provide anticonvulsant compositions which are highly active by the oral route and contain as the essential ingredient certain aminoalkylpyridines and use of these aminoalkylpyridines as potent orally active nonneurotoxic antiepileptic drugs in the treatment of convulsive disorders such as epilepsy.

Other objects and advantages of the present invention include use of the aminoalkylpyridines in the treatment of stroke and other neurological disorders such as Alzheimer's disease, by virtue of their action as noncompetitive NMDA antagonists and as inhibitors of the excitatory neurotransmitter L-glutamate.

In satisfaction of the foregoing objects and advantages, there are provided by this invention aminoalkylpyridine compounds which are useful as anticonvulsant drugs. These compounds may be characterized by the following general formulae:

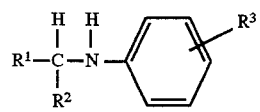

wherein $R^1$ is 4-pyridyl or 3-pyridyl, $R^2$ is hydrogen or methyl and $R^3$ is 3,4-dichloro, p-or m-chloro, p-bromo, p-fluoro, p-lower alkyl, p-lower alkoxy or hydrogen.

Also provided by this invention are orally active, nontoxic anticonvulsant compositions comprising as the active ingredient, a compound selected from those of the following formulae:

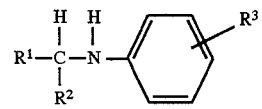

wherein $R^1$ is 4-pyridyl or 3-pyridyl, $R^2$ is hydrogen or methyl and $R^3$ is 3,4-dichloro, p- or m-chloro, p-bromo, p-fluoro, p-lower alkyl, p-lower alkoxy or hydrogen.

Also provided are methods for administration of the anticonvulsant compositions of this invention to mammals including animals and humans in the treatment of convulsive disorders such as epilepsy including partial and generalized seizures.

BRIEF DESCRIPTION OF THE DRAWING

Reference is now made to the drawing accompanying the application which is a graph showing the inhibitory effect of the aminoalkylpyridines of the invention on endogenous glutamate release.

DESCRIPTION OF PREFERRED EMBODIMENTS

As indicated above, this invention relates to several new compounds belonging to two groups of aminoalkylpyridines, which are useful as antiepileptic agents. One group of aminoalkylpyridines of this invention are 1-anilino-1-pyridylethans when $R^2$ is methyl, and the second group of aminoalkylpyridines are 1-anilino-1-pyridylmethans when $R^2$ is hydrogen. The aminoalkylpyridines of this invention are substituted in the 1-position of the alkyl moiety by a 4-pyridyl or 3-pyridyl group and also by an anilino group (aminophenyl group) and this in turn also contains substituents. The alkyl moiety comprises a one-carbon methyl or two-carbon ethyl group. The aminoalkylpyridine compounds of this invention have potent oral anticonvulsant activity as antiepileptic drugs in the treatment of convulsive disorders such as epilepsy including partial seizures and generalized seizures.

In one aspect of the present invention, two groups of compounds are provided which have potent oral antiepileptic activity and which are of the following general formulae:

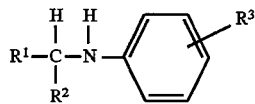

In the above formulae, $R^2$ is hydrogen or methyl and leads to the two groups of aminoalkylpyridines. When $R^2$ is hydrogen, $R^1$ is 4-pyridyl and $R^3$ is 3,4-dichloro, p- or m-chloro, p-bromo, p-fluoro, p-methyl, p-methoxy, or hydrogen. When $R^2$ is methyl, $R^1$ can be 4-pyridyl or 3-pyridyl and $R^3$ can be 3,4-dichloro, p- or m-chloro, p-bromo, p-fluoro, p-methyl, p-methoxy, or hydrogen. Those compounds wherein $R^1$ is 4-pyridyl, $R^2$ is methyl or hydrogen and $R^3$ is 3,4-dichloro, p- or m-chloro, p-bromo, p-fluoro, p-methyl, p-methoxy or hydrogen are new and novel compounds.

In a second aspect of the invention, there are provided novel anticonvulsant compositions which are orally active and nontoxic, and which comprise as the active ingredient an effective amount of a compound selected from those of the following formulae:

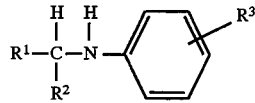

wherein $R^1$ is 4-pyridyl or 3-pyridyl, $R^2$ is hydrogen or methyl and $R^3$ is 3,4-dichloro, p- or m-chloro, p-bromo, p-fluoro, p-methyl, p-methoxy, or hydrogen.

There are further provided by this invention methods for administration of the anticonvulsant composition to mammals including animals and humans.

In a third aspect of this invention, there are provided aminoalkylpyridine compounds of the formulae:

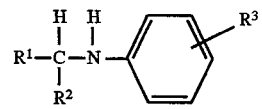

wherein $R^1$ is 4-pyridyl or 3-pyridyl, $R^2$ is hydrogen or methyl, and $R^3$ is 3,4-dichloro, p-chloro, m-chloro, p-bromo, p-fluoro or hydrogen. These compounds selectively inhibit the specific binding of [$^3$H]DTG to the σ (sigma) receptor sites on the NMDA receptor complex and also impair the release of L-glutamate, the excitatory amino acid neurotransmitter. Thus, new aminoalkylpyridine compounds of the above formulae are noncompetitive NMDA antagonists and σ receptor blockers (Choi, Cerebrovas. Brain Metab. Revs. 2, 105–147, 1990). These aminoalkylpyridine compounds of the above formulae are also useful in the treatment of stroke and Alzheimer's disease, by virtue of the action of the above aminoalkylpyridines as inhibitors of L-glutamate release and as noncompetitive NMDA antagonists.

Studies by the Applicant on the metabolism and pharmacology of triazoline anticonvulsants, led to the evolution and discovery of the aminoalkyl heterocycles as a unique class of anticonvulsant agents, superior to the triazolines themselves. [P. K. Kadaba, U.S. Pat. Nos. 4,511,572; 4,618,681; 4,689,334; 4,610,994; 4,820,721]. Work on the aminoalkylpyridines indicate they are nontoxic, and highly effective by the oral route, with protective indices greater than 20. They impair presynaptic release of L-glutamate and also function as noncompetitive NMDA (N-methyl-D-aspartate) antagonists that inhibit with great selectivity and specificity, the sigma receptor, but show no affinity for PCP receptors. NMDA receptor overstimulation by glutamate is implicated in epileptogenesis and epilepsy. Thus, NMDA antagonists also provide prophylaxis and seizure protection. There is a definite need for safer, orally active NMDA antagonists, to afford effective therapies for the epilepsies. Excessive levels of glutamate are suspected not only in epilepsy, but in several other neurological disorders, eg. stroke. Thus, nontoxic, orally active NMDA antagonists developed from aminoalkyl heterocycles, have good potential for commercial application as clinically useful antiepileptic drugs and also as neuroprotective agents in other neurological disorders.

This invention relates to novel, new and previously unknown σ (sigma) selective aminoalkylpyridines, as a unique class of noncompetitive NMDA receptor antagonists, their methods of preparation, and compositions for their use as a novel class of antiepileptic drugs in the treatment of convulsive disorders such as epilepsy including partial and generalized seizures.

Considerable evidence has accrued in the last decade and a half implicating amino acids in chemical neurotransmission; while GABA (gamma-aminobutyric acid) and glycine serve as inhibitory neurotransmitters, L-glutamate and L-aspartate function as excitatory neurotransmitters in the central nervous system [Foster, A. C. and Fagg, G. E. Brain Res. Rev. 7, 103 (1984)]. There exist considerable data that suggest excitatory amino acids (EAAs) may be critically involved in both epileptogenesis and as a focus for the mechanism of action of anticonvulsants (Meldrum, B. S., and Chapman, A. G., In "Glutamine, Glutamate, and GABA in the Central Nervous System," L. Hertz, et. al., Ed., Alan R. Liss, Inc., New York 1983, pp. 625–641; R. Schwarcz and Yehezkel-Ben-Ari, Eds. "Excitatory Amino Acids and Epilepsy", Plenum Press, New York, 1986). Because brain function in the normal state is a dynamic balance of excitatory and inhibitory processes, one would think that excessive neuronal activity leading to seizures may result from either an increase in excitatory transmission, or, alternately, from a decrease in inhibitory transmission. Thus, effecting changes in the concentrations of either excitatory or inhibitory neurotransmitters at their synapses would represent potential mechanisms of anticonvulsant action and strategies for anticonvulsant drug design.

Strong evidence exists for the prominent role of EAAs in excitatory transmission along limbic circuits which are believed to be particularly relevant to kindling epileptogenesis. More recently, evidence for a causal connection between EAA release and onset of hyperactivity has been provided by the use of specific EAA receptor antagonists in various models of epilepsy [Watkins, J. C., and Evans, R. H. Ann. Rev. Pharmacol. Toxicol., 21, 165 (1981)]. There is mounting evidence that the excitatory neurotransmitters, L-glutamate and L-aspartate, play a key role in the spread of epileptic activity from one brain region to another and may also be contributing to its initiation (Meldrum, B. S., In "Handbook of Experimental Pharmacology: Antiepileptic Drugs," H. H. Frey and D. Janz Ed., Berlin, 1984). EAA agonists are convulsants and EAA antagonists show anticonvulsant activity in a variety of seizure models.

EAA Neurotransmitter Systems and the NMDA Receptor-Ionophore Complex. Recent attention has focused on the role of EAAs and the NMDA receptor in health and disease. [Cavalheiro, E. A., Lehmann, J., and Turski, L. Eds., "Frontiers in Excitatory Amino Acid Research", A. R. Liss, New York, N.Y., 1988; Cotman, C. W., et al., J. NIH Res., 1, 65 (1989); Dingledine, R. et al., CRC Crit. Rev. Neurobiol., 4, 1 (1988); Johnson, G., Ann. Rep. Med. Chem., 24, 41 (1989)]. The postsynaptic actions of L-glutamate are believed to be mediated by at least three receptor subtypes named after the prototypical agonists N-methyl-D-aspartate (NMDA), kainate (KA) and quisqualate (QA). Although NMDA itself is not present in the brain, endogenous L-glutamate has the highest affinity for the NMDA receptor. The NMDA receptor is the best characterized of the three EAA receptor subtypes. A group of unusual characteristics sets the NMDA receptor apart from other glutamate receptors, among them, a high $Ca^{2+}$ conductance, a slow onset of the response, and, most important, a voltage-dependent $Mg^{2+}$ blockade of the ionic channel gated by the NMDA receptor. Furthermore, NMDA receptors are associated with, and influenced by, three additional types of binding sites, a PCP (the anesthetic and psychotomimetic drug phencyclidine) binding site that is located within the receptor-associated ion channel, thereby blocking channel conductance, a strychnine-insensitive glycine binding site that is distinct from the inhibitory glycine receptor of the spinal cord and a polyamine recognition site [Williams, K., Romano, C., and Molinoff, P. R., Mol. Pharmacol., 36, 575 (1989)]. Several convincing arguments exist to support the concept that PCP receptors may constitute three subreceptor sites, MK-801, PCP and σ sites, each with a high degree of selectivity and specificity to the respective ligands, MK-801, TCP (a PCP analogue with a thienyl group in place of the phenyl) and DTG.

NMDA receptor overstimulation by high levels of L-glutamate has been implicated in epileptogenesis and epilepsy. NMDA receptor antagonists that block the action of L-glutamate, and thus the overstimulation of the NMDA receptor, may represent novel antiepileptic agents that can afford both prophylaxis as well as seizure protection. NMDA receptor antagonists can be separated into two major groups, competitive and noncompetitive. The competitive NMDA antagonists are usually long chain amino acids of low lipid solubility and poor blood brain barrier penetration and compete for binding at glutamate recognition sites on the NMDA receptor complex [Honore, T., Med. Res. Rev., 9, 1 (1989)]. The noncompetitive NMDA antagonists, on the other hand, comprise a variety of different lipid soluble structures that include ketamine, phencyclidine, benzomorphan "σ opiates" and MK-801. These compounds associate with the PCP site within the NMDA receptor activated membrane channel and thus impede cation $Ca^{2+}$ flow through the channel [Choi, D. W., Cerebrovas. Brain Metab. Revs., 2, 105–147 (1990)]. Thus, by definition, the sigma selective aminoalkylpyridines may function as noncompetitive NMDA antagonists.

The aminoalkylpyridines constitute a unique class of triazoline metabolite analogues; unlike the hydrophilic β-amino alcohol/α-amino acid metabolites of triazolines, these hydrophobic metabolite analogues are potent orally active anticonvulsant agents. Furthermore, neurochemical studies indicate that the ability of the β-amino alcohol to interact with the NMDA receptor and that of the triazoline structure to impair presynaptic release of L-glutamate, are both retained to the full extent or better in the aminoalkylpyridines. Receptor binding studies indicate that while the general site of activity of the aminoalkylpyridines is still confined to the PCP receptor sites, the specificity and selectivity, unlike that of the β-amino alcohol, are no longer at the MK-801 sites, but shifted toward the σ receptor sites of the PCP receptors.

The compounds of the present invention are useful in pharmaceutical compositions using conventional pharmaceutical carriers or vehicles for administration to humans and animals in unit dosage forms, such as tablets, capsules, pills, powders, granules, suppositories, sterile parenteral solutions or suspensions, sterile non-parenteral solutions or suspensions, oral solutions or suspensions, oil in water or water in oil emulsions and the like, containing suitable quantities of the active ingredient.

The aminoalkylpyridines of this invention may be prepared by reaction of pyridine aldehydes, when $R^2$ is hydrogen, or acyl pyridines, when $R^2$ is methyl, ethyl or phenyl, with anilines and reduction of the resulting novel intermediate imines with sodium borohydride as shown in Equation 1.

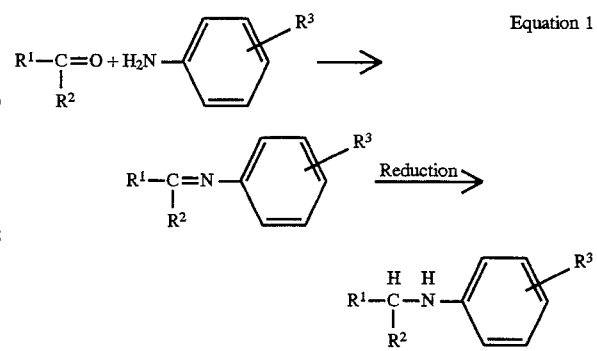

In the above equation, $R^1$, $R^2$ and $R^3$ are as defined above.

In the method of preparation, the reaction between the pyridine aldehydes or ketones and anilines is carried out by condensing the appropriate aniline and pyridine aldehyde or ketone, in an organic solvent such as an aromatic hydrocarbon which can be benzene, toluene and xylene. The reaction is conducted at an elevated temperature ranging from about 50° C. to the boiling point of the solvent used optionally under pressure. Preferably the reaction is conducted in the presence of a catalyst such as an aluminosilicate catalyst including commercially available molecular sieves.

After formation of the imine by this reaction, the reduction to the aminoalkylpyridines is carried out preferably using an alcoholic solvent and a reducing agent such as sodium borohydride. The reaction is conducted with agitation at a temperature of from 60° C. up to the boiling point of the solvent used. The product is then recovered as a solid.

The following examples are presented to illustrate the invention, but it is not to be considered as limited thereto. In the examples and throughout the specification, parts are by weight unless otherwise indicated.

EXAMPLE 1

Preparation of 1-(anilino)-1-(pyridyl)-ethans (1-anilino-1-ethylpyridines)

(a) Preparation of the imines:

A mixture of the appropriate acetylpyridine (0.06 mol) and aniline (0.06 mol) in xylene (150 ml) was refluxed for 4 hours in the presence of molecular sieves (75 g) (Davison, grade 514, effective pore size 4A, 8–12 mesh beads). At the end of the reaction, the molecular sieves were filtered, washed with benzene and the combined filtrates rotary evaporated to remove xylene. The syrupy residual material was crystallized from benzene or benzene-petroleum ether mixture to yield the pure imines in yields varying from 40% to 60%

The imines that were prepared according to the above described procedure are given in Table 1 along with their melting points.

(b) Sodium borohydride reduction of imines. To a solution of the imine (0.03 mol) in ethanol (100 ml) was added finely powdered sodium borohydride (0.15 mol) and the reaction mixture refluxed with magnetic stirring for 2–4 hours.

The reaction mixture was then cooled in ice and the excess sodium borohydride was destroyed by slow addition of dilute hydrochloric acid (1:1 mixture), until the reaction mixture was acidic and no more hydrogen evolution was noticed. The white inorganic solids that precipitated were dissolved by addition of water and the solution made basic to sodium hydroxide. It was then cooled in the refrigerator for 1–2 days, when the 1-anilino-1-ethylpyridines appeared as white to beige colored solids. They were filtered, washed well with water, and recrystallized from acetone-petroleum ether mixture or tertiary-butyl methyl ether and petroleum ether mixture. In Table 2, melting points and yields are given for all the new 1-(anilino)-1-(pyridyl)-ethan compounds prepared.

EXAMPLE 2

Preparation of 1-(anilino)-1-(pyridyl)-methans (anilino methylpyridines)

(a) Preparation of the imines. A mixture of the pyridine aldehyde (0.05 mol) and aniline (0.05 mol) in ethanol was heated on a steam bath, when the imine appeared as a solid mass which was crystallized from ethanol-water mixture. [Kadaba, P. K., *J. Heterocycl. Chem.*, 12, 143 (1975)].

(b) Sodium borohydride reduction of the above imines was carried out according to the procedure described for the preparation of the 1-anilino-1-ethylpyridines.

TABLE 1

| Imine Prepared | Melting point, °C. |
|---|---|
| (1) from 3,4-dichloroaniline and 4-acetylpyridine | 102–104 |
| (2) from 4-chloroaniline and 4-acetylpyridine | 162–165 |
| (3) from 3-chloroaniline and 4-acetylpyridine | 80–82.5 |
| (4) from 4-bromoaniline and 4-acetylpyridine | 157–159.5 |
| (5) from 4-fluoroaniline and 4-acetylpyridine | 133–135 |
| (6) from p-toluidine and 4-acetylpyridine | 80–82 |
| (7) from p-anisidine and 4-acetylpyridine | 111–113 |
| (8) from aniline and 4-acetylpyridine | 81–84.5 |
| (9) from 4-chloroaniline and 3-acetylpyridine | 72–74 |

TABLE 2

| Compound | Melting Point, °C. | Yield, % |
|---|---|---|
| (1) 1-(3,4-Dicloroanilino)-1-(4-pyridyl)-ethan | 153–155.5 | 68 |
| (2) 1-(4-Chloroanilino)-1-(4-pyridyl)-ethan | 104–106 | 79 |
| (3) 1-(3-Chloroanilino)-1-(4-pyridyl)-ethan | 156–158 | 80 |
| (4) 1-(4-Bromoanilino)-1-(4-pyridyl)-ethan | 107–108 | 34 |
| (5) 1-(4-Fluoroanilino)-1-(4-pyridyl)-ethan | 85–87 | 60 |
| (6) 1-(4-Methylanilino)-1-(4-pyridyl)-ethan | 93–95.5 | 72 |
| (7) 1-(4-Methoxyanilino)-1-(4-pyridyl)-ethan | 74.5–76 | 70 |
| (8) 1-(Anilino)-1-(4-pyridyl)-ethan | 126–128 | 60 |
| (9) 1-(4-Chloroanilino)-1-(3-pyridyl)-ethan | 121–123 | 63 |
| (10) 1-(3,4-Dichloroanilino)-1-(4-pyridyl)-methan | 99–101.5 | 31 |
| (11) 1-(4-Chloroanilino)-1-(4-pyridyl)-methan | 91–94 | 26 |
| (12) 1-(3-Chloroanilino)-1-(4-pyridyl)-methan | 82–84 | 18 |
| (13) 1-(4-Bromoanilino)-1-(4-pyridyl)-methan | 92–94.5 | 32 |
| (14) 1-(4-Fluoroanilino)-1-(4-pyridyl)-methan | 67–70 | 33 |
| (15) 1-(4-Methylanilino)-1-(4-pyridyl)-methan | 71–73 | 38 |
| (16) 1-(4-Methoxyanilino)-1-(4-pyridyl)-methan | 74.5–76 | 33 |

The compounds in Table 1 and Table 2 were identified through their elemental analyses, melting points, and NMR spectra (for Table 2 compounds) which show a characteristic doublet of a quartet for the CH proton, when $R^2$ is methyl and a simple doublet of the $CH_2$ group when $R^2$ is hydrogen, in the 4.3–4.5 δ region.

EXAMPLE 3

The aminoalkylpyridine compounds and the resulting orally effective anticonvulsant compositions of this invention are useful in the treatment of convulsive disorders. The oral potency of the compounds range from those which are very highly potent to those of good medium potency, with no accompanying toxicity. A series of aminoalkylpyridines of this invention has been evaluated for anticonvulsant activity by the intraperitoneal (i.p.) and by the oral (p.o.) route using two standard seizure models in the mouse and in the rat, the maximal electroshock seizure (MES) test and the subcutaneous pentylenetetrazol (Metrazole) seizure threshold (scMet) test. These two methods of seizure provocation reliably elicit well characterized seizure phenomena and together they have been shown sufficient to identify all compounds known to demonstrate anticonvulsant activity in other tests [Porter, R. J., et al., Cleveland Clinic Quarterly, 51, 293 (1984)]. Based on the screening results, the compounds are placed in one of three categories. Those failing to demonstrate anticonvulsant activity at doses up to 300 mg/kg are considered inactive. Class II compounds show anticonvulsant activity at doses greater than 100 mg/kg or show activity at 100 mg/kg which is not reinforced by similar activity at 300 mg/kg. Thus, compounds of class or group II demonstrate anticonvulsant activity without signs of neurological deficit, but do not have significant potency. The Class I compounds are those which are most promising as anticonvulsants. They demonstrate anticonvulsant activity in either the MES test or the scMet test, or both at doses of 100 mg/kg or 30 mg/kg without signs of neurological deficit and this have an estimated protective index of greater than 1.

Neurotoxicity is determined by the rotorod ataxia test in mice and by the positional sense test and gait and stance test in the rat.

The following Table 3 presents the results of these anticonvulsant tests with respect to several compounds of the present invention. This Table 3 identifies the specific compounds tested by chemical name and provides the route of administration, the animal species used, and the anticonvulsant activity based on classification in Group I or Group II, when intraperitoneally administered, and based on percent protection, when orally administered.

As shown in Table 3, all the aminoalkylpyridine compounds belong to Class I and demonstrate anticonvulsant activity at doses of 30 mg/kg to 100 mg/kg, without signs of neurological deficit. The anticonvulsant activity of the compounds is far more pronounced in the MES test than in the scMet test, in both mice and rats, by the i.p. and oral routes of administration, and protective indices greater than 20 are obtained by oral administration in the rat.

Anticonvulsant quantification in mice, i.p., for 6 compounds (Table 4) further confirms the greater potency of the aminoalkylpyridines in the MES test; in the scMet test, protection is obtained only at high dose levels nearing toxic doses. Anticonvulsant quantification in rats, p.o. (Table 5) clearly shows that the aminoalkylpyridines, as a class, are ineffective in the scMet test, but evince a remarkably high degree of anticonvulsant activity by the oral route in the MES seizure model, with P.I. values >20.

The potent activity of the aminoalkylpyridines in the MES test is of great significance, because drugs used in the treatment of the two major types of seizures (partial and generalized) are quite distinct in their clinical effects. They also fall into two pharmacological classes even though seizures may be induced experimentally by a wide variety of methods. The clinical aspects of certain generalized seizures, especially absence seizures, are highly correlated with experimental seizures produced in the scMet model. Likewise, partial seizures in humans correlate positively with experimental seizures elicited by the MES test (Porter, R. J., and Pitlick, W. H., In "Basic and Clinical Pharmacology", 4th Ed., B. G. Katzung Ed., Appleton & Lange, C. A., 1989, pp. 287–303).

TABLE 3

| Compound | ASP Group Classification (i.p. mouse) | Percent protection* at 50 mg/kg dose, p.o., in the MES Test in the rat |
|---|---|---|
| (1) 1-(3,4-Dicloroanilino)-1-(4-pyridyl)-ethan | I | — |
| (2) 1-(4-Cloroanilino)-1-(4-pyridyl)-ethan | I | 75–100 |
| (3) 1-(3-Chloroanilino)-1-(4-pyridyl)-ethan | I | 50–75 |
| (4) 1-(4-Bromoanilino)-1-(4-pyridyl)-ethan | I | 75–100 |
| (5) 1-(4-Fluoroanilino)-1-(4-pyridyl)-ethan | I | 75–100 |
| (6) 1-(4-Methylanilino)-1-(4-pyridyl)-ethan | I | — |
| (7) 1-(4-Methoxyanilino)-1-(4-pyridyl)-ethan | I | 25–50 |
| (8) 1-(Anilino)-1-(4-pyridyl)-ethan | I | 50–75 |
| (9) 1-(4-Chloroanilino)-1-(3-pyridyl)-ethan | I | 25–75 |
| (10) 1-(3,4-Dichloroanilino-1-(4-pyridyl)-methan | I | 50 |
| (11) 1-(4-Chloroanilino)-1-(4-pyridyl)-methan | I | 50–100 |
| (12) 1-(3-Chloroanilino)-1-(4-pyridyl)-methan | I | >50 |
| (13) 1-(4-Bromoanilino)-1-(4-pyridyl)-methan | I | >50 |
| (14) 1-(4-Fluoroanilino-1-(4-pyridyl)-methan | I | 25 |
| (15) 1-(4-Methylanilino)-1-(4-pyridyl)-methan | I | — |
| (16) 1-(4-Methoxyanilino)-1-(4-pyridyl)-methan | I | — |

*Number of animals protected/number of animals tested is defined as percent protection.

TABLE 4

Anticonvulsant Quantification in Mice, i.p.

| | Compound | Time of Test (h)[a] | ED$_{50}$, mg/kg MES | ScMet | TD$_{50}$ mg/kg (rotorod) | P.I.[d] MES |
|---|---|---|---|---|---|---|
| (2) | 1-(4-Chloroanilino)-1-(4-pyridyl)-ethan | 0.25, 0.25 0.25 | 53.71 (51.61–57.34)[b] [31.40 ± 9.80][c] | <150 | 160.11 (130.87–187.59) [9.81 ± 2.95] | 2.98 |
| (3) | 1-(3-Chloroanilino)-1- | 1, 1 | 95.45 | >250 | >500 | >5.24 |

TABLE 4-continued

Anticonvulsant Quantification in Mice, i.p.

| Compound | Time of Test (h)[a] | ED$_{50}$, mg/kg MES | ED$_{50}$, mg/kg ScMet | TD$_{50}$ mg/kg (rotorod) | P.I.[d] MES |
|---|---|---|---|---|---|
| (4-pyridyl)-ethan | 24 | (71.99–113.3) [8.50 ± 2.96] | | | |
| (4) 1-(4-Bromoanilino)-1-(4-pyridyl)-ethan | 4, 4 0.25 | 62.74 (50.60–80.48) [5.42 ± 1.56] | >200 | >200 | >3.19 |
| (5) 1-(4-Fluoroanilinol)-1-(4-pyridyl)-ethan | 0.25, 0.5 0.25 | 57.42 (50.94–66.55) [12.36 ± 3.67] | >80 | 141.1 (117.5–171.9) | 2.46 [9.55 ± 3.04] |
| (8) 1-(Anilino)-1-4-pyridyl)-ethan | 0.5, 0.5 0.25 | 81.74 (72.94–96.81) [11.17 ± 3.55] | <300 | 161.0 (125.8–194.9) | 1.97 [6.84 ± 2.05] |
| (11) 1-(4-Chloroanilino)-1-(4-pyridyl)-methan | 0.5, 0.5 0.25 | 68.43 (63.16–76.43) [20.43 ± 6.81] | 106.9 (80.28–140.10) [6.07 ± 1.58] | <225 | <3.3 |

[a]Time of test is given in the order for MES, scMet, and rotorod
[b]( ) 95% confidence interval
[c][ ] Slope, regression line ± standard error
[d]P.I. = TD$_{50}$/ED$_{50}$

TABLE 5

Anticonvulsant Quantification in Rat, p.o.

| Compound | Time of Test (h)[a] | ED$_{50}$, mg/kg MES | ED$_{50}$, mg/kg ScMet | TD$_{50}$ mg/kg | P.I.[d] MES |
|---|---|---|---|---|---|
| (2) 1-(4-Chloroanilino)-1-(4-pyridyl)-ethan | 2, 2, 0.25 thru 24 | 22.89 (14.40–32.70)[b] [3.17 ± 1.19][c] | >250 | >470 | >20.53 |
| (4) 1-(4-Bromoanilinol)-1-(4-pyridyl)-ethan | 4, 4, 1 | 20.89 (16.76–26.13) [6.88 ± 2.43] | >250 | >500 | >23.93 |
| (5) 1-(4-Fluoroanilino)-1-(4-pyridyl)-ethan | 0.5, 0.5, 0.25 thru 24 | 81.06 (53.82–132.5) [2.94 ± 0.99] | >250 | >500 | >6.17 |
| (8) 1-(Anilino)-1-(4-pyridyl)-ethan | 0.5, 0.5, 0.25 thru 24 | 48.40 (33.12–77.60) [3.61 ± 1.23] | >250 | >500 | >10.33 |
| (11) 1-(4-Chloroanilino)-1-(4-pyridyl)-methane | 4, 4, 0.25 thru 24 | 39.14 (24.30–58.65) [2.85 ± 0.74] | >250 | >500 | >12.8 |

[a]Time of test given in the order for MES, scMet, and rotorod
[b]( ) 95% confidence interval
[c][ ] Slope, regression line ± standard error
[d]P.I. = TD$_{50}$/ED$_{50}$ The anticonvulsant compounds of the present invention may be administered to animals or humans at doses ranging from about 15 mg/kg up to about 200 mg/kg. Preferred levels of administration range from about 15 mg/kg up to 100 mg/kg. The active ingredients or compounds of this invention may be administered in any desired form by injection or in the oral form. Conventional adjuvents and carriers may be employed in combination with about 0.001 to 2.0 wt. % of the active ingredient. Thus, the anticonvulsant compositions of this invention may be administered in pill form or by injection. As indicated above, the dosage rate ranges from about 15 mg/kg up to about 200 mg/kg.

Screening Methodology to Determine Anticonvulsant Activity: In mice, i.p.: All compounds are solubilized in 0.5% methylcellulose. The solvent has been tested for anticonvulsant and toxic effects and found to introduce no significant bias into the testing of anticonvulsant activity. The compounds are administered intraperitoneally in a volume of 0.01 ml/gm to male Carworth Farms #1 mice weighing about 20 gm. All compounds are tested at least at three dose levels (30, 100 an 300 mg/kg) at 30 minutes and 4 hours after their administration.

The Maximal Electroshock Seizure Test (MES): Maximal electroshock seizures are elicited with a 60 Hz alternating current of 50 mA intensity in mice and about 150 mA in rats (5–7 times that necessary to elicit minimal electroshock seizures), delivered for 0.2 sec via corneal electrodes. A drop of 0.9% saline is instilled in the eye prior to application of the electrodes in order to prevent the death of the animal. Abolition of the hind limb tonic extension component of the seizure is defined as protection and results are expressed as number of animals protected/number of animals tested.

The Subcutaneous Pentylenetetrazol (Metrazole) Seizure Threshold Test (scMet): A 0.5% solution of 85 mg/kg of pentylenetetrazol is administered subcutaneously in the posterior midline. The animal is observed for 30 minutes. Failure to observe even a threshold seizure (a single episode of clonic spasms of at least 5 sec duration) is defined as protection and the results are expressed as number of animals protected/number of animals tested.

Neurotoxicity is evaluated in mice by the rotorod ataxia test. The animal is placed on a wooden rod of 1⅛" diameter rotating at 6 rpm. Normal mice can remain on a rod rotating at this speed indefinitely. Neurologic toxicity is defined as the failure of the animal to remain on the rod for 1 minute and is expressed as number of animals exhibiting toxicity/number of animals tested.

Anticonvulsant Quantification in Mice, i.p.: The ED$_{50}$ values are determined in the MES, scMet and rotorod ataxia test. To determine the $ED_{50}$ values, five logarithmically spaced doses of the test compound are administered to animals in groups of ten, to cover 0–100% protection, and the dose required to protect 50% of the animals ($ED_{50}$) together with its 95% confidence limits, are determined graphically.

Anticonvulsant Quantification in Rats p.o.: Substances which exhibit unusual potential as possible antieptileptic drugs, as determined from all prior testing will be subjected to anticonvulsant activity test in the rat (Sprague-Dawley strain). This species will be subject of the complete anticonvulsant quantification test evaluation as described above, but after oral (gavage) administration of the candidate compound. These results will permit the critical comparison of the anticonvulsant activity and neurotoxicity of the agent under study with similar data previously obtained in mice. Substances which exhibit potential antiepileptic activity will be advanced for toxicity and selected pharmacology studies.

Neurological deficit in rats is examined by the positional sense test and gait and stance test. In the positional sense test, one hind leg is gently lowered over the edge of a table, whereupon the animal will quickly lift it back to normal position. Inability to do so rapidly indicates a neurologic deficit. In the gait and stance test, a neurologic deficit is indicated by a circular or zigzag gait, ataxia, abnormal spread of the legs, abnormal body posture, tremor, hyperactivity, lack of exploratory behavior, somnolence, stupor, or catalepsy.

EXAMPLE 4

EAAs are known to play important roles in excitatory neurotransmission in partial seizures as discussed earlier. Evaluation of potential displacement activity of aminoalkylpyridine compounds 1, 2, 3, 4, 5, 6, 8, 9, 10, 11, 12 and 13 at all inhibitory and excitatory amino acid receptor types and subtypes using appropriate radioligands, according to known procedures indicated that aminoalkylpyridines inhibit selectively the binding of [$^3$H]DTG, a ligand highly specific for the σ (sigma) receptor population of the PCP receptors on the NMDA receptor-ionophore complex (Weber et al., Proc. Nat. Acad. Sci., 83, 8784 (1986)]. They show no activity at the [$^3$H]MK-801- or [$^3$H]TCP-binding receptor sites of the PCP receptor. The aminoalkylpyridines also inhibit $Ca^{2+}$ dependent, $K^+$ evoked release of endogenous L-glutamate in guinea pig cerebrocortical slices. Thus, several aminoalkylpyridines of this invention are effective antagonists of NMDA-receptor mediated EAA neurotransmission and function as noncompetitive NMDA antagonists and thus can be used to advantage in epilepsy, stroke and Alzheimer's disease.

Aminoalkylpyridines Attenuate EAA Neurotransmission: Role as Noncompetitive NMDA Antagonists: There are several approaches to antagonizing glutamate-mediated excitatory processes, and glutamate neurotoxicity. Based on Choi's speculative consideration of glutamate neurotoxicity as a sequential three-stage process—induction, amplification and expression—a range of measures might be used to protect neurons from excitotoxic damage, since each step of the neurotoxic process is specifically amenable to therapeutic interference [Choi, D. W., Cerebrovas. Brain Metab. Revs., 2, 105–147 (1990)]. Blockade of induction, i.e. overstimulation of glutamate receptors inducing intracellular accumulation of $ca^{2+}$, might be accomplished most easily by antagonizing postsynaptic glutamate receptors, as also by reducing glutamate release from presynaptic terminals.

EAAs are known to play important roles in excitatory transmission in partial seizures as discussed earlier. In general, antieptileptic drugs effective against MES seizures alter ionic transport across excitable membranes [Porter, R. J., and Pitlick, W. H., In "Basic and Clinical Pharmacology", 4th Edn., B. G. Katzung, Ed., Appleton and Lange, CA 1989, pp. 287–303]. Based on this rationale, the aminoalkylpyridines may be expected to attenuate EAA neurotransmission. Indeed, evaluation of potential displacement activity of #2 at all inhibitory and excitatory amino acid receptor types and subtypes using appropriate radioligands, indicate that this aminoalkylpyridine inhibits at 10 μM concentration, 49% of the binding of [$^3$H]DTG, a ligand highly specific for the σ (sigma) receptor population of the PCP receptors on the NMDA receptor-ionophore complex (Table 6). It shows no activity at the [$^3$H]MK-801- or [$^3$H]TCP-binding receptor sites of the PCP receptor. The aminoalkylpyridine (#2) also inhibits $Ca^{2+}$ dependent, $K^+$ evoked release of endogenous L-glutamate in guinea pig cerebrocortical slices to an extent of 74% at 50 μM and 80% at 100 μM concentrations, comparable to the parent ADD17014 (Table 6). Because aminoalkylpyridines in general are highly effective in the MES seizure model, these compounds, as a class can be expected to be effective antagonists of NMDA-receptor mediated EAA neurotransmission. The ability of the aminoalkylpyridines to selectively inhibit the σ receptor sites, in addition to impairing presynaptic release of L-glutamate, offers potential for their use as noncompetitive NMDA antagonists to afford protection against epilepsy, particularly, partial seizures including complex partial seizures where there is a definite need for more effective drugs, as discussed earlier.

The Therapeutic Potential of Aminoalkylpyridines as Clinically Useful Antiepileptic Drugs: Potent Orally Active, Nonneurotoxic Anticonvulsant Agents: The aminoalkylpyridines have evolved as a result of studies on the metabolism and pharmacology of the 1,2,3-triazoline anticonvulsants. They are highly lipophilic molecules that can readily cross the blood brain barrier. In screening experiments using animal seizure models, they show a high degree of anticonvulsant activity by the oral route with no attendant neurotoxicity, and with P.I. values >20. When compared with the respective parent triazolines, the aminoalkylpyridines appear to be superior anticonvulsant agents (see Table 8 for comparison of data). Unlike the rigid, closed ring structures of the triazolines and aziridines, the flexible, open structures of the aminoalkylpyridines show inhibitory activity at postsynaptic NMDA receptors while also fully retaining the ability of the parent to impair presynaptic release.

TABLE 6

Inhibition of specific binding of radioligands at EAA - receptors by aminoalkyl-4-pyridine (#2)

| Receptor/ Selectivity | Radio ligand | Reference Compound | Reference Ki (nM) | Percent Inhibition (Average; N = 2) | |
|---|---|---|---|---|---|
| | | | | $10^{-7}$M | $1.0^{-5}$M |
| Adenosine | | | | | |
| Adenosine | | MECA | 39.50 | –15.2 | –15.9 |
| Amino Acids | | | | | |
| Excitatory | | | | | |
| Glycine | [$^3$H]glycine | D-Alanine | 4900.00 | 8.7 | –4.0 |
| Kainate | [$^3$H]KA | Kainic Acid | 24.93 | –3.7 | –7.3 |
| MK-801 | [$^3$H]MK-801 | MK-801 | 4.30 | 13.5 | 17.0 |
| NMDA | [$^3$H]CGS19755 | CPP | 359.00 | 3.5 | –6.6 |
| PCP | [$^3$H]TCP | PCP | 62.30 | –3.8 | –1.8 |

5,648,369

TABLE 6-continued

Inhibition of specific binding of radioligands at EAA - receptors by aminoalkyl-4-pyridine (#2)

| Receptor/Selectivity | Radio ligand | Reference Compound | Reference Ki (nM) | Percent Inhibition (Average; N = 2) $10^{-7}$M | $1.0^{-5}$M |
|---|---|---|---|---|---|
| Quisqualate | [$^3$H]AMPA | AMPA | 11.80 | 4.2 | 4.3 |
| Sigma Inhibitory | [$^3$H]DTG | Haloperidal | 11.50 | 12.9 | 49.1 |
| Benzodiazepine | | Clonazepam | 3.40 | −4.7 | −7.8 |
| GABA$_A$ | | Muscimol | 2.80 | 6.5 | 1.2 |
| GABA$_e$ | | Baclofen | 176.00 | 3.6 | −4.9 |
| Glycine | | Strychnine Nitrate | 33.50 | −1.8 | −1.4 |

Values are expressed as the percent inhibition of specific binding and represent the average of duplicate tubes at each of the concentrations tested.

TABLE 7

Inhibition of L-glutamate release by ADD17014 and 1-(4-chloroanilino)-1-ethyl-4-pyridine (#2)

Effects of drugs: Results are shown on the attached figure and in the table below. All results are means ± SEM of n = 4 independent experiments performed in triplicate.
Release of endogenous gluatamate in the presence of ADD17014 and #2 and 30 mM K$^+$, significantly different from effects of K$^+$ alone (P < 0.001).

| Treatment | Release (% basal) |
|---|---|
| basal 2 | 108 ± 2 |
| 30 mM K$^+$ | 184 ± 10 |
| ADD17014 | |
| 50 μM (basal) | 101 ± 9 |
| 50 μM (K$^+$) | 136 ± 6 |
| 100 μM (basal) | 109 ± 4 |
| 100 μM (K$^+$) | 122 ± 5 |
| Aminoalkylpyridine #2 | |
| 50 μM (basal) | 101 ± 6 |
| 50 μM (K$^+$) | 121 ± 8 |
| 100 μM (basal) | 99 ± 9 |
| 100 μM (K$^+$) | 114 ± 4 |

TABLE 8

Comparison of Anticonvulsant Efficacy of Triazolines with Aminoalkylpyridines in the MES Test, Rat, p.o.

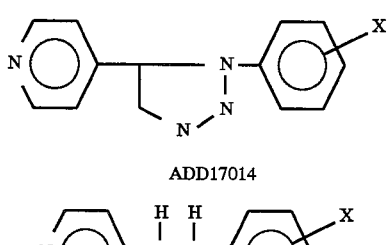

ADD17014

| X | | |
|---|---|---|
| 4-Cl | 265.76 | 22.89 |
| 4-CH$_3$ | Class II (ASP | Class I (ASP |

TABLE 8-continued

| | classification, active at 300 mg/kg only) | classification active at 100 mg/kg) |
|---|---|---|
| 4-OCH$_3$ | Class III (ASP classification, not active up to 300 mg/kg) | Class I (ASP 25–50% protection at 50 mg/kg |
| H | Class II (ASP classification, active at 300 mg/kg only) | 48.40 |

This invention has been described herein with reference to certain preferred embodiments. However, as obvious variations thereon will become apparent to those skilled in the art, the invention is not to be considered as limited thereto.

What is claimed is:

1. A compound of the following formulae:

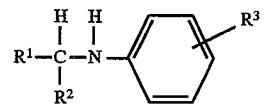

wherein R$^1$ is 4-pyridyl, R$^2$ is hydrogen or methyl and R$^3$ is p-methyl or p-methoxy.

2. A compound according to claim 1 wherein R$^2$ is methyl and R$^3$ is p-methyl.

3. A compound according to claim 1 wherein R$^2$ is methyl and R$^3$ is p-methoxy.

4. A compound according to claim 1 wherein R$^2$ is hydrogen and R$^3$ is p-methyl.

5. A compound according to claim 1 wherein R$^2$ is hydrogen and R$^3$ is p-methoxyl.

6. A potent orally active, nonneurotoxic anticonvulsant composition comprising as the active ingredient, an anticonvulsant effective amount of a compound selected from the group consisting of those of the formulae:

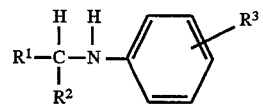

wherein R$^1$ is 4-pyridyl, R$^2$ is hydrogen or methyl and R$^3$ is p-methyl or p-methoxy, and a pharmaceutical carrier.

7. A composition according to claim 6 wherein R$^1$ is 4-pyridyl, R$^2$ is methyl and R$^3$ is p-methyl.

8. A composition according to claim 6 wherein R$^1$ is 4-pyridyl, R$^2$ is methyl and R$^3$ is p-methoxy.

9. A composition according to claim 6 wherein R$^1$ is 4-pyridyl, R$^2$ is hydrogen and R$^3$ is p-methyl.

10. A composition according to claim 6 wherein R$^1$ is 4-pyridyl, R$^2$ is hydrogen and R$^3$ is p-methoxy.

11. A potent orally active, nonneurotoxic anticonvulsant composition comprising as the active ingredient, an anticonvulsant effective amount of a compound of the formulae

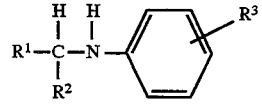

wherein R$^1$ is 4-pyridyl, R$^2$ is methyl and R$^3$ is p-chloro, and a pharmaceutical carrier.

12. A potent orally active, nonneurotoxic anticonvulsant composition comprising as the active ingredient, an anticonvulsant effective amount of a compound of the formulae

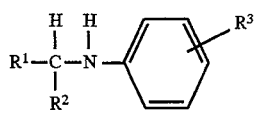

wherein $R^1$ is 3-pyridyl, $R^2$ is methyl and $R^3$ is p-chloro, and a pharmaceutical carrier.

13. A composition according to claim 6 wherein a sufficient amount of the effective ingredient is contained in said composition to provide a dosage amount ranging from about 15 mg/kg to 200 mg/kg.

14. A method for the treatment of convulsive disorders in mammals which comprises administration thereto of an effective dosage amount of an anticonvulsant composition of claim 6.

15. A method according to claim 14 wherein the composition is administered in a dosage amount ranging from about 15 mg/kg to 200 mg/kg of body weight.

16. An inhibitor of excitatory amino acid (EAA) neurotransmission which comprises inhibition of L-glutamate release and NMDA/sigma receptor blocking, comprising an effective amount of a compound of the following formulae:

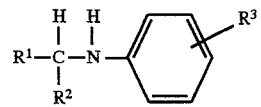

wherein $R^1$ is 4-pyridyl or 3-pyridyl, $R^2$ is hydrogen or methyl and $R^3$ is p-methyl or p-chloro and a pharmaceutical carrier.

17. An EAA inhibitor and noncompetitive NMDA antagonist/σ receptor blocker composition according to claim 16, wherein $R^1$ is 4-pyridyl, $R^2$ is methyl and $R^3$ is p-chloro.

18. An EAA inhibitor and noncompetitive NMDA antagonist/σ receptor blocker composition according to claim 16, wherein $R^1$ is 4-pyridyl, $R^2$ is methyl and $R^3$ is p-methyl.

19. An EAA inhibitor and noncompetitive NMDA antagonist/σ receptor blocker composition according to claim 16, wherein $R^1$ is 3-pyridyl, $R^2$ is methyl and $R^3$ is p-chloro.

20. An imine of the formula:

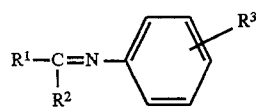

wherein $R^1$ is 4-pyridyl or 3-pyridyl, $R^2$ is hydrogen or methyl, and $R^3$ is 3,4-dichloro, p-chloro, m-chloro, p-bromo, p-fluoro, p-lower alkyl, p-lower alkoxy or hydrogen.

21. An imine according to claim 20 wherein $R^1$ is 4-pyridyl, $R^2$ is methyl and $R^3$ is 3,4-dichloro, p-chloro, m-chloro, p-bromo, p-fluoro, p-methyl, p-methoxy or hydrogen.

22. A composition according to claim 6 wherein the active ingredient is contained in the composition in an amount of 0.001 to 2.0 wt. %.

* * * * *